United States Patent
Depalma et al.

(10) Patent No.: US 10,564,087 B2
(45) Date of Patent: Feb. 18, 2020

(54) METHODS FOR QUANTIFYING PARTICULATES IN CELL CULTURE

(71) Applicant: CELULARITY, INC., Warren, NJ (US)

(72) Inventors: Lauren M. Depalma, Port Murray, NJ (US); Daniel Dewitt, Morristown, NJ (US); Li Ren, Basking Ridge, NJ (US)

(73) Assignee: Celularity, Inc., Warren, NJ (US)

( * ) Notice: Subject to any disclaimer, the term of this patent is extended or adjusted under 35 U.S.C. 154(b) by 0 days.

(21) Appl. No.: 15/505,343

(22) PCT Filed: Sep. 11, 2015

(86) PCT No.: PCT/US2015/049621
§ 371 (c)(1),
(2) Date: Feb. 21, 2017

(87) PCT Pub. No.: WO2016/040766
PCT Pub. Date: Mar. 17, 2016

(65) Prior Publication Data
US 2017/0268978 A1    Sep. 21, 2017

Related U.S. Application Data

(60) Provisional application No. 62/049,895, filed on Sep. 12, 2014.

(51) Int. Cl.
*C12N 5/00* (2006.01)
*G01N 15/06* (2006.01)
*G01N 15/00* (2006.01)

(52) U.S. Cl.
CPC . *G01N 15/0618* (2013.01); *G01N 2015/0069* (2013.01); *G01N 2015/0693* (2013.01)

(58) Field of Classification Search
CPC .............................. C12N 5/00; G01N 15/0618
See application file for complete search history.

(56) References Cited

U.S. PATENT DOCUMENTS

| | | | | |
|---|---|---|---|---|
| 5,356,814 A | * | 10/1994 | Carrico, Jr. | C12M 45/02 422/504 |
| 2004/0241653 A1 | * | 12/2004 | Feinstein | C12Q 1/6886 435/6.14 |
| 2006/0193874 A1 | * | 8/2006 | Jones | A61K 39/105 424/234.1 |

OTHER PUBLICATIONS

Sharif et al. "The Dual ROle of Paramagnetic Particles for Integrated Lysis and Measurement in a Rapid Immunoassay for Intracellular Proteins", IEEE Transactions on Biomedical Engineering, vol. 60, No. 5, May 2013, 1209-1217 (Year: 2013).*
Fuller et al., "Automated Three-Dimensional Characterization of Osteoclastic Resorption Lacunae by Stereoscopic Scanning Electron Microscopy", J of Bone and Mineral Research, vol. 9, No. 1, 1994, 917-23 (Year: 1994).*

* cited by examiner

*Primary Examiner* — Ruth A Davis
(74) *Attorney, Agent, or Firm* — Celularity, Inc.; Geoffry T. Knudsen

(57) ABSTRACT

Provided are methods for quantifying and/or detecting sub-visible particulates in cell cultures. Specifically, the methods comprise a step of breaking down, e.g., lysing, cells in a cell culture. The methods can further comprising filtering the cell culture through a filter. Further provided are methods of quantifying sub-visible particulates that do not pass through the filter using a microscope.

14 Claims, 1 Drawing Sheet

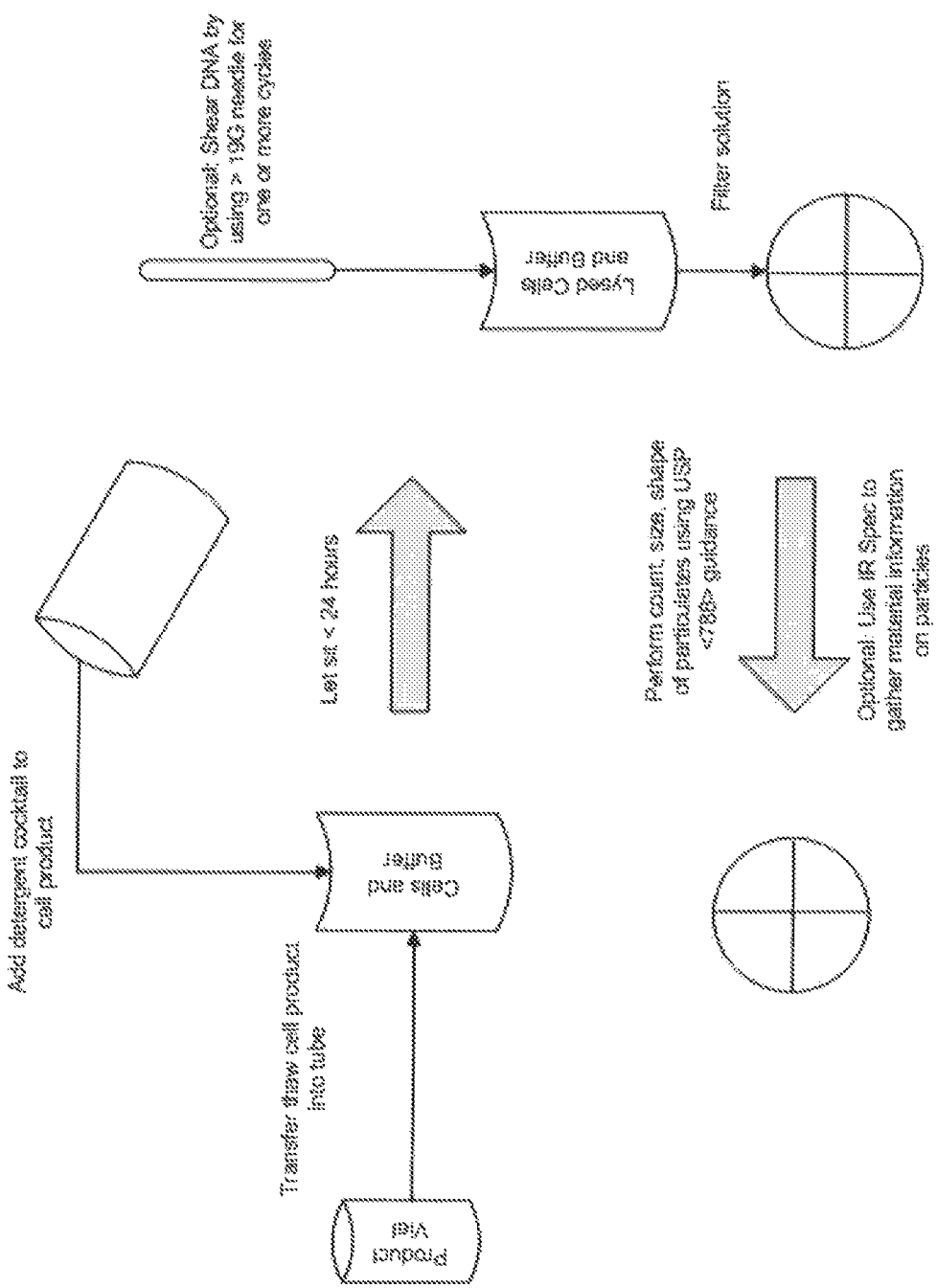

METHODS FOR QUANTIFYING PARTICULATES IN CELL CULTURE

This application is a national stage entry of International Patent Application No. PCT/US2015/049621, filed Sep. 11, 2015, which claims the benefit of U.S. Provisional Patent Application No. 62/049,895, filed Sep. 12, 2014, the disclosure of each of which is incorporated herein by reference in its entirety.

1. INTRODUCTION

Provided herein are methods for quantifying and/or detecting sub-visible particulates in cell cultures.

2. BACKGROUND

Methods have been established to characterize and quantify sub-visible particulates in injectable drug products. See United States Pharmacopeia <788> Particulate Matter in Injections. However, the United States Pharmacopeia-recommended assays for assessing sub-visible particulates in injectable drug products are not applicable to cell therapies, as cells themselves can be considered particulates. Accordingly, there remains a need in the art for methods of quantifying sub-visible particulates in cell cultures.

3. SUMMARY

Provided herein are methods for quantifying and/or detecting sub-visible particulates in cell cultures. The methods provided herein allow for the determination of the presence of non-cell sub-visible particulates in cell cultures, i.e., sub-visible particulates that are not intact cells, and quantification of such sub-visible particulates. The methods provided herein comprise a step of breaking down, e.g., lysing, cells in a cell culture. By breaking down the cells in the cell culture, non-cell sub-visible particulates can readily be detected and quantified. Therefore, advantageously, the methods provided herein allow for the detection and quantification of sub-visible particulates in cell culture, wherein, for example, said sub-visible particulates are the same size as or similar in size to the cells in the cell culture. One of skill in the art will recognize that once sub-visible particulates in a given cell culture are quantified, the number of sub-visible particulates can be extrapolated to other cell cultures in, e.g., the same lot of cells.

Bioreactors are often used to produce large amounts of cells. Many types of cells are adherent, and thus require a growth platform during production. Thus, to mass-produce adherent cells in bioreactors, the adherent cells often are cultured with microcarriers, which provide the cell growth platform. However, microcarriers and fragments thereof, known as fines, often remain in the cell cultures they are used to produce, even when methods are employed to remove them before final formulation of the cell culture. These foreign particulates can be problematic when cells are formulated for therapeutic use, as they can cause injury to the subjects receiving the cell therapy. Thus, it is important to be able to quantify microcarriers and fragments thereof (fines) in cell cultures produced using microcarriers. The methods provided herein allow for such quantification.

The methods provided herein for quantifying sub-visible particulates in cell cultures comprise breaking down, e.g., lysing, the cells in the cell culture and determining the number of sub-visible particulates in the cell culture. FIG. 1 provides a schematic of an exemplary method of the invention. In certain embodiments, the cell culture has been produced in a bioreactor. In certain embodiments, the cell culture has been produced in a bioreactor, processed to remove particulates (e.g., microcarriers), and formulated as a therapeutic. In certain embodiments, the cell culture is part of a lot of cells, i.e., the cell culture is one of several units (individual cell cultures) produced from a larger cell culture (e.g., a cell culture produced in a bioreactor). In certain embodiments, the cell culture comprises microcarriers and/or microcarrier fines.

The methods provided herein can be used to quantify sub-visible particulates in cell cultures of any type, i.e., cell cultures comprising any type of cell. See Section 5.1. In certain embodiments, the cell culture is formulated for therapeutic use. In certain embodiments, the cell culture is formulated for experimental use, e.g., use in a laboratory.

In certain embodiments, the methods provided herein are performed on cells taken directly from a cell culture lot, e.g., before cell culture units are prepared from the cell culture lot, and the number of sub-visible particulates detected in the cell culture lot are extrapolated to represent the number of sub-visible particulates in the cell culture lot, e.g., as a whole or on a concentration basis (e.g., the number of sub-visible particulates per ml of the cell culture lot).

In certain embodiments, the methods provided herein are performed on individual cell culture units from a cell culture lot, and the number of sub-visible particulates detected in the cell culture unit are extrapolated to represent the number of sub-visible particulates in other cell culture units of the cell culture lot. In certain embodiments, cell culture units obtained at various points of production of a cell culture lot (e.g., the beginning, middle, and end of production) are subjected to the methods described herein to determine the representative number of sub-visible particulates in the other cell culture units of the cell culture lot. See Example 1.

In certain embodiments, the methods provided herein are performed on individual cell culture units from a cell culture lot, without destroying the cell culture unit, i.e., the cell culture unit can later be used for its intended purpose (e.g., as a therapeutic). In accordance with such embodiments, a portion of a unit to be tested is removed from the unit and subjected to a method described herein. Therefore, sub-visible particulates in individual cell culture units of a cell culture lot can be quantified using the methods described herein. In a specific embodiment, cell culture units in a cell culture lot are produced so that they comprise a volume that is larger than the volume of cells necessary for the intended use of the cells. For example, a cell culture unit formulated for use as a therapeutic, wherein the therapeutic comprises cells in 1 ml of solution, can be produced so that it comprises 1.1 ml of solution (with the same concentration of cells). Prior to use of the cell culture unit, the 1.1 ml of solution can be mixed, 0.1 ml of the solution can be removed, and sub-visible particulates in the 0.1 ml of solution can be quantified. The number of sub-visible particulates detected in the 0.1 ml of solution then can be used to determine the total number of sub-visible particulates in the cell culture unit. In accordance with such methods, any amount of solution from a cell culture unit can be removed for analysis, e.g., about 1%, 5%, 10%, 20%, 30%, 40%, or 50% of solution can be removed for analysis or about 1-5%, 5-10%, 10-20%, 20-30%, 30-40%, or 40-50% of solution can be removed for analysis. See Example 2.

In certain embodiments, the cells in a cell culture to be analyzed using the methods provided herein are lysed using a solution (e.g., a lysis buffer) that comprises one or more detergents, e.g., Triton-X-100, sodium dodecyl sulfate (SDS), sodium deoxycholate, and/or NP-40. In certain embodiments, the cells in a cell culture to be analyzed using the methods provided herein are lysed by osmotic lysis. In certain embodiments, the cells in a cell culture to be analyzed using the methods provided herein are lysed by sonication. In certain embodiments, the cells in a cell culture to be analyzed using the methods provided herein are lysed by subjecting the cell culture to one or more freeze-thaw cycles. Exemplary methods of cell lysis are described in Section 5.2. In certain embodiments, the cells in a cell culture to be analyzed using the methods provided herein are not lysed using a mechanical lysis method.

Once the cells in a cell culture to be analyzed using the methods provided herein are broken down, the number of sub-visible particulates in the cell culture can be quantified using any method known in the art for particulate quantification. See Section 5.3. In certain embodiments, sub-visible particulates from the cell culture are quantified microscopically, e.g., using a stereoscope. In certain embodiments, the sub-visible particulates are quantified using a stereoscope that comprises a graticule, which allows for quantification of particulates of a desired size (e.g., particulates greater than 10 µm or greater than 25 µm in size).

In certain embodiments, after the cells in a cell culture being analyzed are broken down (e.g., lysed) and prior to quantification of the sub-visible particulates in the cell culture, the solution comprising the cell culture is passed through a syringe to further break down cellular components, e.g., DNA. For example, a syringe comprising, e.g., a 19 gauge or smaller needle, can be used to draw up the solution comprising the cell culture, and the drawn-up solution then can be injected back into the container comprising the solution. This process can be repeated multiple times.

In certain embodiments, after the cells in a cell culture being analyzed are broken down (e.g., lysed) and prior to quantification of the sub-visible particulates in the cell culture, the solution comprising the cell culture is passed through a filter. Filters of particular size can be selected based on the threshold size of sub-visible particulate desired to be quantified. For example, a 0.45 µm filter can be utilized to quantify sub-visible particulates greater than 0.45 µm in size, e.g., sub-visible particulates 2 µm in size or greater. In certain embodiments, a gridded filter (i.e., a filter comprising one or more grids) is used to filter the cell culture. In accordance with such embodiments, the sub-visible particulates that do not pass through the filter are quantified and represent the number of sub-visible particulates that are at least a certain size (i.e., a size greater than the threshold of the filter).

The methods provided herein can be used to determine amounts of sub-visible particulates of any size threshold in cell culture. For example, to quantify sub-visible particulates greater than 10 µm in a cell culture, a 10 µm pore size filter can be utilized in the filtration step of a method described herein. As another example, to quantify sub-visible particulates greater than 25 µm in a cell culture, a 25 µm pore size filter can be utilized in the filtration step of a method described herein. Exemplary filters that can be used in accordance with the methods described herein include filters having the following pore sizes: 0.025 µm, 0.05 µm, 0.1 µm, 0.22 µm, 0.3 µm, 0.45 µm, 0.65 µm, 0.8 µm, 1.2 µm, 3.0 µm, 5.0 µm, 8.0 µm, 10.0 µm, 15.0 µm 20.0 µm, and 25.0 µm. Alternatively, or in addition, as discussed above, particulate size can be assessed using a microscope (e.g., a stereoscope) that comprises a graticule, which allows for quantification of particulates of a desired size.

In certain embodiments, the sub-visible particulates quantified using the methods provided herein are further analyzed, e.g., to analyzed determine the type of particulate quantified. Methods for classifying types of particulates are known in the art, e.g., Fourier transform infrared spectroscopy (FTIR) and Raman spectroscopy, and can be used in conjunction with the methods described herein. See Section 5.4.

In a specific embodiment, provided herein is a method for quantifying sub-visible particulates in a cell culture, said method comprising, in order: (i) lysing the cells in the cell culture, e.g., using a detergent-containing lysis buffer; and (ii) quantifying the number of sub-visible particulates. In a specific embodiment, the cell culture comprises microcarriers, or fines thereof. In another specific embodiment, sub-visible particulates from the cell culture are quantified microscopically, e.g., using a stereoscope.

In a specific embodiment, provided herein is a method for quantifying sub-visible particulates in a cell culture, said method comprising, in order: (i) lysing the cells in the cell culture, e.g., using a detergent-containing lysis buffer; (ii) filtering the cell culture; and (iii) quantifying the number of sub-visible particulates that do not pass through the filter. In a specific embodiment, the cells in the cell culture are produced using microcarriers. In another specific embodiment, the cells in the cell culture are lysed using a lysis buffer that comprises Triton-X-100 and SDS. In another specific embodiment, the filter is a gridded filter. In another specific embodiment, sub-visible particulates from the cell culture are quantified microscopically, e.g., using a stereoscope, by counting the sub-visible particulates present on the filter. In another specific embodiment, the filter is a gridded filter and sub-visible particulates from the cell culture are quantified microscopically, e.g., using a stereoscope, by counting the sub-visible particulates present on the grids of the gridded filter. In another specific embodiment, the number of sub-visible particulates that passes through the filter is quantified, e.g., as an alternative to or in addition to quantifying the number of sub-visible particulates that do not pass through the filter.

In another specific embodiment, provided herein is a method for quantifying sub-visible particulates in a cell culture, said method comprising, in order: (i) lysing the cells in the cell culture, e.g., using a detergent-containing lysis buffer; (ii) passing the solution comprising the cell culture through a syringe to further break down cellular components; (iii) filtering the cell culture; and (iv) quantifying the number of sub-visible particulates that do not pass through the filter. In a specific embodiment, the cells in the cell culture are produced using microcarriers. In another specific embodiment, the cells in the cell culture are lysed using a lysis buffer that comprises Triton-X-100 and SDS. In another specific embodiment, the syringe comprises a 19 gauge or smaller needle. In another specific embodiment, the filter is a gridded filter. In another specific embodiment, sub-visible particulates from the cell culture are quantified microscopically, e.g., using a stereoscope, by counting the sub-visible particulates present on the filter. In another specific embodiment, the filter is a gridded filter and sub-visible particulates from the cell culture are quantified microscopically, e.g., using a stereoscope, by counting the sub-visible particulates present on the grids of the gridded filter. In another specific embodiment, the number of sub-visible particulates that passes through the filter is quantified, e.g., as an alternative to or in addition to quantifying the number of sub-visible particulates that do not pass through the filter.

3.1 Terminology

As used herein, the term "microcarrier" refers to a substrate that supports the growth of adherent cells, e.g., when grown in liquid suspension.

As used herein, the term "cell culture" refers to a solution comprising cells that have been cultured, e.g., expanded in culture. Cell cultures, as used herein, can be cell culture lots produced in a bioreactor, or can be cells suitable for administration to a subject, e.g., a human subject, e.g., in the form of a therapeutic.

As used herein, the term "cell culture lot" refers to a group of individual cell culture units derived from a source. For example, a cell culture lot can be generated by producing a large volume cell culture in a bioreactor, and aliquoting the cell culture into cell culture units.

As used herein, the term "cell culture unit" refers to an individual unit of cells belonging to a cell culture lot, e.g., a vial of cells among a cell culture lot that comprises multiple vials of cells.

As used herein, the term "about," when used in conjunction with a number, refers to any number within ±1, ±5 or ±10% of the referenced number.

4. BRIEF DESCRIPTION OF THE DRAWINGS

FIG. 1 depicts an exemplary method for detection of sub-visible particulates in cell culture.

5. DETAILED DESCRIPTION

Provided herein are methods for quantifying and/or detecting sub-visible particulates in cell cultures. Generally, the term sub-visible particulate is meant to refer to particulates that are not cells, and that range in size from 10 µm-20 µm, 20 µm-30 µm, 30 µm-40 µm, 50 µm-100 µm, 100 µm-150 µm, 150 µm-200 µm, 200 µm-250 µm, or 250 µm-300 µm. The methods provided herein allow for the determination of the presence of non-cell sub-visible particulates in cell cultures, i.e., sub-visible particulates that are not intact cells, and quantification of such sub-visible particulates. The methods provided herein comprise a step of breaking down, e.g., lysing, cells in a cell culture. By breaking down the cells in the cell culture, non-cell sub-visible particulates can readily be detected and quantified. Therefore, advantageously, the methods provided herein allow for the detection and quantification of sub-visible particulates in cell culture, wherein, for example, said sub-visible particulates are the same size as or similar in size to the cells in the cell culture. One of skill in the art will recognize that once sub-visible particulates in a given cell culture are quantified, the number of sub-visible particulates can be extrapolated to other cell cultures in, e.g., the same lot of cells.

Bioreactors are often used to produce large amounts of cells. Many types of cells are adherent, and thus require a growth platform during production. Thus, to mass-produce adherent cells in bioreactors, the adherent cells often are cultured with microcarriers, which provide the cell growth platform. However, microcarriers and fragments thereof, known as fines, often remain in the cell cultures they are used to produce, even when methods are employed to remove them before final formulation of the cell culture. These foreign particulates can be problematic when cells are formulated for therapeutic use, as they can cause injury to the subjects receiving the cell therapy. Thus, it is important to be able to quantify microcarriers and fragments thereof (fines) in cell cultures produced using microcarriers. The methods provided herein allow for such quantification.

The methods provided herein for quantifying sub-visible particulates in cell cultures comprise breaking down, e.g., lysing, the cells in the cell culture and determining the number of sub-visible particulates in the cell culture. FIG. 1 provides a schematic of an exemplary method of the invention. In certain embodiments, the cell culture has been produced in a bioreactor. In certain embodiments, the cell culture has been produced in a bioreactor, processed to remove particulates (e.g., microcarriers), and formulated as a therapeutic. In certain embodiments, the cell culture is part of a lot of cells, i.e., the cell culture is one of several units (individual cell cultures) produced from a larger cell culture (e.g., a cell culture produced in a bioreactor). In certain embodiments, the cell culture comprises microcarriers and/or microcarrier fines.

The methods provided herein can be used to quantify sub-visible particulates in cell cultures of any type, i.e., cell cultures comprising any type of cell. See Section 5.1. In certain embodiments, the cell culture is formulated for therapeutic use. In certain embodiments, the cell culture is formulated for experimental use, e.g., use in a laboratory.

In certain embodiments, the methods provided herein are performed on cells taken directly from a cell culture lot, e.g., before cell culture units are prepared from the cell culture lot, and the number of sub-visible particulates detected in the cell culture lot are extrapolated to represent the number of sub-visible particulates in the cell culture lot, e.g., as a whole or on a concentration basis (e.g., the number of sub-visible particulates per ml of the cell culture lot).

In certain embodiments, the methods provided herein are performed on individual cell culture units from a cell culture lot, and the number of sub-visible particulates detected in the cell culture unit are extrapolated to represent the number of sub-visible particulates in other cell culture units of the cell culture lot. In certain embodiments, cell culture units obtained at various points of production of a cell culture lot (e.g., the beginning, middle, and end of production) are subjected to the methods described herein to determine the representative number of sub-visible particulates in the other cell culture units of the cell culture lot. See Example 1.

In certain embodiments, the methods provided herein are performed on individual cell culture units from a cell culture lot, without destroying the cell culture unit, i.e., the cell culture unit can later be used for its intended purpose (e.g., as a therapeutic). In accordance with such embodiments, a portion of a unit to be tested is removed from the unit and subjected to a method described herein. Therefore, sub-visible particulates in individual cell culture units of a cell culture lot can be quantified using the methods described herein. In a specific embodiment, cell culture units in a cell culture lot are produced so that they comprise a volume that is higher than the volume of cells necessary for the intended use of the cells. For example, a cell culture unit formulated for use as a therapeutic, wherein the therapeutic comprises cells in 1 ml of solution, can be produced so that it comprises 1.1 ml of solution (with the same concentration of cells). Prior to use of the cell culture unit, the 1.1 ml of solution can be mixed, 0.1 ml of the solution can be removed, and sub-visible particulates in the 0.1 ml of solution can be quantified. The number of sub-visible particulates detected in the 0.1 ml of solution then can be used to determine the total number of sub-visible particulates in the cell culture unit. In accordance with such methods, any amount of solution from a cell culture unit can be removed for analysis, e.g., about 1%, 5%, 10%, 20%, 30%, 40%, or 50% of solution can be removed for analysis or about 1-5%, 5-10%, 10-20%, 20-30%, 30-40%, or 40-50% of solution can be removed for analysis. See Example 2.

In certain embodiments, the cells in a cell culture to be analyzed using the methods provided herein are lysed using a solution (e.g., a lysis buffer) that comprises one or more detergents, e.g., Triton-X-100, sodium dodecyl sulfate (SDS), sodium deoxycholate, and/or NP-40. In certain embodiments, the cells in a cell culture to be analyzed using the methods provided herein are lysed by osmotic lysis. In certain embodiments, the cells in a cell culture to be analyzed using the methods provided herein are lysed by sonication. In certain embodiments, the cells in a cell culture to be analyzed using the methods provided herein are lysed by subjecting the cell culture to one or more freeze-thaw cycles. Exemplary methods of cell lysis are described in Section 5.2.

Once the cells in a cell culture to be analyzed using the methods provided herein are broken down, the number of sub-visible particulates in the cell culture can be quantified using any method known in the art for particulate quantification. See Section 5.3. In certain embodiments, sub-visible particulates from the cell culture are quantified microscopically, e.g., using a stereoscope. In certain embodiments, the sub-visible particulates are quantified using a stereoscope that comprises a graticule, which allows for quantification of particulates of a desired size (e.g., particulates greater than 10 µm or greater than 25 µm in size).

In certain embodiments, after the cells in a cell culture being analyzed are broken down (e.g., lysed) and prior to quantification of the sub-visible particulates in the cell culture, the solution comprising the cell culture is passed through a syringe to further break down cellular components, e.g., DNA. For example, a syringe comprising, e.g., a 19 gauge or smaller needle, could be used to draw up the solution comprising the cell culture, and the drawn-up solution then can be injected back into the container comprising the solution. This process can be repeated multiple times.

In certain embodiments, after the cells in a cell culture being analyzed are broken down (e.g., lysed) and prior to quantification of the sub-visible particulates in the cell culture, the solution comprising the cell culture is passed through a filter. Filters of particular size can be selected based on the threshold size of sub-visible particulate desired to be quantified. For example, a 0.45 µm filter can be utilized to quantify sub-visible particulates greater than 0.45 µm in size, e.g., visible particulates 2 µm in size or greater. In certain embodiments, a gridded filter (i.e., a filter comprising one or more grids) is used to filter the cell culture. In accordance with such embodiments, the sub-visible particulates that do not pass through the filter are quantified and represent the number of sub-visible particulates that are at least a certain size (i.e., a size greater than the threshold of the filter).

The methods provided herein can be used to determine amounts of sub-visible particulates of any size threshold in cell culture. For example, to quantify sub-visible particulates greater than 10 µm in a cell culture, a 10 µm pore size filter can be utilized in the filtration step of a method described herein. As another example, to quantify sub-visible particulates greater than 25 µm in a cell culture, a 25 µm pore size filter can be utilized in the filtration step of a method described herein. Exemplary filters that can be used in accordance with the methods described herein include filters having the following pore sizes: 0.025 µm, 0.05 µm, 0.1 µm, 0.22 µm, 0.3 µm, 0.45 µm, 0.65 µm, 0.8 µm, 1.2 µm, 3.0 µm, 5.0 µm, 8.0 µm, 10.0 µm, 15.0 µm 20.0 µm, and 25.0 µm. Alternatively, or in addition, as discussed above, particulate size can be assessed using a microscope (e.g., a stereoscope) that comprises a graticule, which allows for quantification of particulates of a desired size.

In certain embodiments, the sub-visible particulates quantified using the methods provided herein are further analyzed, e.g., to analyzed determine the type of particulate quantified. Methods for classifying types of particulates are known in the art, e.g., Fourier transform infrared spectroscopy (FTIR) and Raman spectroscopy, and can be used in conjunction with the methods described herein. See Section 5.4.

In a specific embodiment, provided herein is a method for quantifying sub-visible particulates in a cell culture, said method comprising, in order: (i) lysing the cells in the cell culture, e.g., using a detergent-containing lysis buffer; and (ii) quantifying the number of sub-visible particulates. In a specific embodiment, the cells in the cell culture are produced using microcarriers. In another specific embodiment, sub-visible particulates from the cell culture are quantified microscopically, e.g., using a stereoscope.

In a specific embodiment, provided herein is a method for quantifying sub-visible particulates in a cell culture, said method comprising, in order: (i) lysing the cells in the cell culture, e.g., using a detergent-containing lysis buffer; (ii) filtering the cell culture; and (iii) quantifying the number of sub-visible particulates that do not pass through the filter. In a specific embodiment, the cells in the cell culture are produced using microcarriers. In another specific embodiment, the cells in the cell culture are lysed using a lysis buffer that comprises Triton-X-100 and SDS. In another specific embodiment, the filter is a gridded filter. In another specific embodiment, sub-visible particulates from the cell culture are quantified microscopically, e.g., using a stereoscope, by counting the sub-visible particulates present on the filter. In another specific embodiment, the filter is a gridded filter and sub-visible particulates from the cell culture are quantified microscopically, e.g., using a stereoscope, by counting the sub-visible particulates present on the grids of the gridded filter. In another specific embodiment, the number of sub-visible particulates that passes through the filter is quantified, e.g., as an alternative to or in addition to quantifying the number of sub-visible particulates that do not pass through the filter.

In another specific embodiment, provided herein is a method for quantifying sub-visible particulates in a cell culture, said method comprising, in order: (i) lysing the cells in the cell culture, e.g., using a detergent-containing lysis buffer; (ii) passing the solution comprising the cell culture through a syringe to further break down cellular components; (iii) filtering the cell culture; and (iv) quantifying the number of sub-visible particulates that do not pass through the filter. In a specific embodiment, the cells in the cell culture are produced using microcarriers. In another specific embodiment, the cells in the cell culture are lysed using a lysis buffer that comprises Triton-X-100 and SDS. In another specific embodiment, the syringe comprises a 19 gauge or smaller needle. In another specific embodiment, the filter is a gridded filter. In another specific embodiment, sub-visible particulates from the cell culture are quantified microscopically, e.g., using a stereoscope, by counting the sub-visible particulates present on the filter. In another specific embodiment, the filter is a gridded filter and sub-visible particulates from the cell culture are quantified microscopically, e.g., using a stereoscope, by counting the sub-visible particulates present on the grids of the gridded filter. In another specific embodiment, the number of sub-visible particulates that passes through the filter is quantified, e.g., as an alternative to or in addition to quantifying the number of sub-visible particulates that do not pass through the filter.

5.1 Cells

In certain embodiments, the methods provided herein are used to quantify sub-visible particulates in a culture of stem cells or progenitor cells. In a specific embodiment, said stem cell or progenitor cells are isolated embryonic stem cells, embryonic germ cells, induced pluripotent stem cells, mesenchymal stem cells, bone marrow-derived mesenchymal stem cells, bone marrow-derived mesenchymal stromal cells, tissue plastic-adherent placental stem cells (PDAC®), umbilical cord stem cells, amniotic fluid stem cells, amnion derived adherent cells (AMDACs), osteogenic placental adherent cells (OPACs), adipose stem cells, limbal stem cells, dental pulp stem cells, myoblasts, endothelial progenitor cells, neuronal stem cells, exfoliated teeth derived stem cells, hair follicle stem cells, dermal stem cells, parthenogenically derived stem cells, reprogrammed stem cells, amnion derived adherent cells, or side population stem cells. In another specific embodiment, said stem cell or progenitor cells are isolated hematopoietic stem cells or hematopoietic progenitor cells.

In another specific embodiment, the methods provided herein are used to quantify sub-visible particulates in a culture of adherent cells, e.g., cells that require a substrate or platform (e.g., tissue culture plastic or microcarriers) to survive and/or proliferate.

In another specific embodiment, the methods provided herein are used to quantify sub-visible particulates in a culture of tissue culture plastic-adherent $CD34^-$, $CD10^+$, $CD105^+$, and $CD200^+$ placental stem cells, e.g., the placental stem cells described in U.S. Pat. Nos. 7,468,276 and 8,057,788, the disclosures of which are hereby incorporated by reference in their entireties.

In another specific embodiment, the methods provided herein are used to quantify sub-visible particulates in a culture of cells of the immune system, e.g., T cells, B cells, dendritic cells, and/or natural killer (NK) cells. In a specific embodiment, said NK cells comprise, or are, $CD56^+$ $CD16^-$ placental intermediate natural killer (PiNK) cells, e.g., the placental NK cells described in US 2009/0252710, the disclosure of which is hereby incorporated by reference in its entirety.

In certain embodiments, the methods provided herein are used to quantify sub-visible particulates in a culture of differentiated cells, e.g., without limitation, endothelial cells, epithelial cells, dermal cells, endodermal cells, mesodermal cells, fibroblasts, osteocytes, chondrocytes, natural killer cells, dendritic cells, hepatic cells, pancreatic cells, or stromal cells. In various more specific embodiments, said differentiated cells are, or comprise salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus luteum cells, granulosa lutein cells, theca lutein cells, juxtaglomerular cell, macula densa cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells, cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epididymal principal cells, epididymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, reticulocytes, megakaryocytes, monocytes, connective tissue macrophages. epidermal Langerhans cells, dendritic cells, microglial cells, neutrophils, eosinophils, basophils, mast cell, helper T cells, suppressor T cells, cytotoxic T cell, natural Killer T cells, B cells, natural killer cells, melanocytes, retinal pigmented epithelial cells, oogonia/oocytes, spermatids, spermatocytes, spermatogonium cells, spermatozoa, ovarian follicle cells, Sertoli cells, thymus epithelial cell, and/or interstitial kidney cells.

5.2 Cell Lysis

The methods provided herein comprise a step of breaking down, e.g., lysing, cells in cell culture.

In a specific embodiment, cells in a cell culture analyzed using a method described herein are lysed using a solution that comprises one or more detergents. Exemplary detergents that can be used in accordance with the methods described herein include, without limitation, Triton-X-100, Triton-X-114, sodium dodecyl sulfate (SDS), sodium deoxycholate, NP-40, ethyl trimethyl ammonium bromide, bile salts (e.g., cholate), CHAPS, CHAPSO, Brij-35, Brij-58, Tween 20, Tween 80, octyl glucoside, octyl thoglucoside, n-Dodecyl-beta-D-Maltoside, and sodium cholate.

When lysing cells using a solution that comprises one or more detergents, varying detergent concentrations can be used. For example, detergent can be used at concentrations of 1-10%, 1-20%, 1-30%, 1-40%, 2-10%, 5-10%, 10-20%, 20-30%, or 30-40%. In certain embodiments, detergent is used at a concentration of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%.

When lysing cells using a solution that comprises one or more detergents, varying ratios of detergent to cell culture (volume:volume) can be used. For example, the ratio of detergent to cell culture can be 1:1, 2:1, 3:1, 4:1, 5:1, 6:1, 7:1, 8:1, 9:1, or 10:1; or can be 1:2, 1:3, 1:4, 1:5, 1:6, 1:7, 1:8, 1:9, or 1:10.

In a specific embodiment, cells in a cell culture analyzed using a method described herein are lysed using a solution that comprises Triton-X 100. In another specific embodiment, said Triton-X 100 is used at a concentration of 2-10%.

In another specific embodiment, cells in a cell culture analyzed using a method described herein are lysed using a solution that comprises SDS. In another specific embodiment, said SDS is used at a concentration of 1-20%.

In another specific embodiment, cells in a cell culture analyzed using a method described herein are lysed using a solution that comprises Triton-X 100 and SDS. In another specific embodiment, said Triton-X 100 is used at a concentration of 2-10% and said SDS is used at a concentration of 1-20%. In another specific embodiment, said solution comprising Triton-X 100 and SDS (e.g., Triton-X 100 at a concentration of 2-10% and SDS at a concentration of 1-20%) is used at a ratio of 10:1 detergent solution to cell culture (volume:volume).

When lysing cells using a solution that comprises one or more detergents, the cell culture/detergent solution can be incubated at any temperature appropriate, e.g., room temperature or under heated conditions, e.g., at 37° C. Further, the cell culture/detergent solution can be incubated for any time deemed appropriate, e.g., 1-2 hours, 2-4 hours, or 4-6 hours. 6-10 hours, 10-15 hours, 15-20 hours, or 20-24 hours. In a specific embodiment, the cell culture/detergent solution is incubated for about 24 hours.

In another specific embodiment, cells in a cell culture analyzed using a method described herein are lysed by osmotic lysis. In accordance with such embodiments, the cells in the cell culture are exposed to an osmotic imbalance, causing excess fluid (e.g., water) to move into the cell, resulting in a hypotonic environment. Once the volume of fluid in the cell exceeds the cell membrane's capacity, the cell bursts.

In another specific embodiment, cells in a cell culture analyzed using a method described herein are lysed by freeze-thaw lysis. According to such methods, cell cultures are frozen then thawed (e.g., at room temperature or 37° C.). The freezing/thawing results in swelling of the cells, which ultimately break open (lyse) as ice crystals form during the freezing process and then contract during thawing. In certain embodiments, cells in a cell culture analyzed using a method described herein are subjected to multiple freeze-thaw cycles.

In another specific embodiment, cells in a cell culture analyzed using a method described herein are lysed by sonication, a method that utilized pulses of high frequency sound to disrupt cell membranes.

5.3 Methods of Particulate Detection

The methods provided herein allow for quantification of sub-visible particulates in cell culture following breaking down, e.g., lysis, of the cells in the cell culture. Once the cells in a cell culture are broken down (e.g., lysed), sub-visible particulates can be quantified using several different methods.

In a specific embodiment, sub-visible particulates are quantified following filtration of the cell culture solution (i.e., after the cells in the cell culture solution have been broken down). In another specific embodiment, the filter used in filtration of the cell culture solution is used in the quantification of the sub-visible particulates in the cell culture. In accordance with this embodiment, a gridded filter can be utilized. Upon filtration, sub-visible particulates that do not filter out of the solution remain on the filter (e.g. the gridded filter), and can be quantified microscopically, e.g., using a stereoscope. The number of sub-visible particulates detected on the filter can be used to determine the number of sub-visible particulates in the cell culture overall, or in a given volume of the cell culture (e.g., how many particulates exist per 1 ml of the cell culture). Such methods further allow for determination of the number of particulates of a certain size in the cell culture, an end point that can easily be selected based on the pore size of the filter selected.

Filters of particular size can be selected based on the threshold size of sub-visible particulate desired to be quantified. For example, a 0.45 μm filter can be utilized to quantify sub-visible particulates greater than 0.45 μm in size, e.g., visible particulates 2 μm in size or greater. In certain embodiments, a gridded filter (i.e., a filter comprising one or more grids) is used to filter the cell culture. In accordance with such embodiments, the sub-visible particulates that do not pass through the filter are quantified and represent the number of sub-visible particulates that are at least a certain size (i.e., a size greater than the threshold of the filter).

The methods provided herein can be used to determine amounts of sub-visible particulates of any size threshold in cell culture. For example, to quantify sub-visible particulates greater than 10 µm in a cell culture, a 10 µm pore size filter can be utilized in the filtration step of a method described herein. As another example, to quantify sub-visible particulates greater than 25 µm in a cell culture, a 25 µm pore size filter can be utilized in the filtration step of a method described herein. Exemplary filters that can be used in accordance with the methods described herein include filters having the following pore sizes: 0.025 µm, 0.05 µm, 0.1 µm, 0.22 µm, 0.3 µm, 0.45 µm, 0.65 µm, 0.8 µm, 1.2 µm, 3.0 µm, 5.0 µm, 8.0 µm, 10.0 µm, 15.0 µm 20.0 µm, and 25.0 µm.

Other methods for quantifying sub-visible particulates can be used in accordance with the methods described herein. In one embodiment, sub-visible particulates in a cell culture, wherein the cells in the cell culture have been broken down as described herein, are detected using the light obscuration particle count test. See United States Pharmacopeia <788> Particulate Matter in Injections. In one embodiment, sub-visible particulates in a cell culture, wherein the cells in the cell culture have been broken down as described herein, are detected using the microscopic particle count test. See United States Pharmacopeia <788> Particulate Matter in Injections.

5.4 Further Analyses

In certain embodiments, the sub-visible particulates quantified using the methods provided herein are further analyzed, e.g., to analyzed determine the type, size, or shape of particulate quantified.

In a specific embodiment, sub-visible particulates detected and quantified using a method described herein are further characterized by Fourier transform infrared spectroscopy (FTIR). In another specific embodiment, sub-visible particulates detected and quantified using a method described herein are further characterized by Raman spectroscopy. In another specific embodiment, sub-visible particulates detected and quantified using a method described herein are further characterized using an automated particle counter, e.g., the Beckman-Coulter MULTISIZER™.

5.7 6. EXAMPLES

Example 1

Sub-Visible Particulate Quantification in Cell Culture

This Example describes a method for quantifying sub-visible particulates in a cell culture lot, wherein individual cell culture units of the cell culture lot are tested and the results are extrapolated to the cell culture lot.

A cell culture lot comprising tissue culture plastic-adherent $CD34^-$, $CD10^+$, $CD105^+$, and $CD200^+$ placental stem cells is mass produced in a bioreactor. Because the placental stem cells are adherent cells, microcarriers are used in the bioreactor production of the cells.

Five liters of placental stem cells are produced in the bioreactor. The placental stem cells are dissociated from the microcarriers by trypsin digestion, and the placental stem cells are isolated. It is determined that the final concentration of placental stem cells is $1 \times 10^8$ cell/ml. Fifty thousand cell culture units are prepared from the lot of placental stem cells. Each cell culture unit comprises 1 ml of placental stem cells, at a concentration of $1 \times 10^8$ cell/ml.

Cell culture units 1 (the first cell culture unit aliquoted), 2,500, and 5,000 are analyzed to quantify the number of sub-visible particulates in each unit. The following method is performed. Each cell culture unit is placed in a flask that contains 10 ml of a lysis solution that comprises 10% Triton-X-100 and 20% SDS. The flask is maintained at room temperature for 24 hours. After the 24 hour period, the contents of the flask are filtered through a gridded filter with a 0.45 µm pore size, followed by one water wash through the filter. The filter is placed on a petri dish to dry, then imaged at 100× magnification using a stereoscope that has two light sources and a graticule to measure particulate size. Particulates 10 µm in size or greater are counted per grid square. The number of particulates counted is extrapolated to provide the total number of particulates on the surface of the filter that are 10 µm in size or greater and thus the total number of particulates present in the cell culture unit that are 10 µm in size or greater. Results obtained for each of cell culture units 1, 2,500, and 5,000 are compared to confirm that the number of particulates present in each cell culture unit that are 10 µm in size or greater is consistent across the cell culture units of the lot.

Example 2

Sub-Visible Particulate Quantification in Cell Culture

This Example describes a method for quantifying sub-visible particulates in a cell culture lot, wherein each cell culture unit of the cell culture lot is prepared so that the number of sub-visible particulates in each cell culture unit can be determined.

A cell culture lot comprising tissue culture plastic-adherent $CD34^-$, $CD10^+$, $CD105^+$, and $CD200^+$ placental stem cells is mass produced in a bioreactor. Because the placental stem cells are adherent cells, microcarriers are used in the bioreactor production of the cells.

Five liters of placental stem cells are produced in the bioreactor. The placental stem cells are dissociated from the microcarriers by trypsin digestion, and the placental stem cells are isolated. It is determined that the final concentration of placental stem cells is $1 \times 10^8$ cell/ml. Forty thousand cell culture units are prepared from the lot of placental stem cells. Each cell culture unit comprises 1.1 ml of placental stem cells, at a concentration of $1 \times 10^8$ cell/ml.

Each cell culture unit is formulated so that the number of sub-visible particulates in each unit can be quantified, if desired. The following method is performed to quantify sub-visible particulates in a cell culture unit. A cell culture unit is selected for analysis, and 0.1 ml of the cell culture unit is placed in a tube that contains 1 ml of a lysis solution that comprises 10% Triton-X-100 and 20% SDS. The tube is maintained at room temperature for 24 hours. After the 24 hour period, the contents of the tube are filtered through a gridded filter with a 0.45 µm pore size, followed by one water wash through the filter. The filter is placed on a petri dish to dry, then imaged at 100× magnification using a stereoscope that has two light sources and a graticule to measure particulate size. Particulates 10 µm in size or greater are counted per grid square. The number of particulates counted is extrapolated to provide the total number of particulates on the surface of the filter that are 10 µm in size or greater and thus the total number of particulates present in the cell culture unit that are 10 µm in size or greater.

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A method for quantifying sub-visible particulates in a cell culture, said method comprising, in order:(i) removing microcarriers from the cell culture, (ii) lysing the cells in the cell culture; and (iii) quantifying the number of sub-visible particulates in the culture, wherein the sub-visible particulates are microcarriers or microcarrier fines.

2. The method of claim 1, wherein said cells are lysed using a solution comprising a detergent.

3. The method of claim 2, wherein said detergent comprises is selected from the group consisting of Triton-X-100, Triton-X114, sodium dodecyl sulfate (SDS), sodium deoxycholate, NP-40, ethyl trimethyl ammonium bromide, bile salts (e.g., cholate), CHAPS, CHAPSO, Brij-35, Brij-58, Tween 20, Tween 80, octyl glucoside, octyl thoglucoside, n-Dodecyl-beta-D-Maltoside, and sodium cholate.

4. The method of claim 1, wherein said cells are lysed using a solution comprising two or more types of detergent.

5. The method of claim 4, wherein said two or more types of detergent are Triton-X100, and sodium dodecyl sulfate (SDS).

6. The method of claim 1, wherein the cell culture was produced in a bioreactor using microcarriers.

7. The method of claim 1, wherein the sub-visible particulates from the cell culture are quantified microscopically.

8. The method of claim 7, wherein the sub-visible particulates from the cell culture are quantified using a stereoscope.

9. The method of claim 1 wherein the cell culture is an entire cell culture unit from a cell culture lot.

10. The method of claim 1, wherein the cell culture is a portion of a cell culture unit.

11. A method for quantifying sub-visible particulates in a cell culture, said method comprising, in order: (i) removing microcarriers from the cell culture, (ii) lysing the cells in the cell culture; (iii) filtering the cell culture; and (iv) quantifying the number of sub-visible particulates that do not pass through the filter, wherein the sub-visible particulates are microcarriers or microcarrier fines.

12. The method of claim 11, wherein the filter is a gridded filter.

13. A method for quantifying sub-visible particulates in a cell culture, said method comprising, in order: (i) removing microcarriers from the cell culture, (ii) lysing the cells in the cell culture; (iii) passing the solution comprising the cell culture through a syringe to further break down cellular components; (iv) filtering the cell culture solution; and (v) quantifying the number of sub-visible particulates that do not pass through the filter, wherein the sub-visible particulates are microcarriers or microcarrier fines.

14. The method of claim 13, wherein said syringe comprises a 19 gauge needle.

* * * * *